(12) United States Patent
Tiefenthaler

(10) Patent No.: US 7,867,448 B2
(45) Date of Patent: *Jan. 11, 2011

(54) OPTICAL SENSOR AND OPTICAL PROCESS FOR THE CHARACTERIZATION OF A CHEMICAL AND/OR BIO-CHEMICAL SUBSTANCE

(75) Inventor: Kurt Tiefenthaler, Zurich (CH)

(73) Assignee: Artificial Sensing Instruments ASI AG, Zurich (CH)

( * ) Notice: Subject to any disclaimer, the term of this patent is extended or adjusted under 35 U.S.C. 154(b) by 1324 days.

This patent is subject to a terminal disclaimer.

(21) Appl. No.: 10/908,945

(22) Filed: Jun. 1, 2005

(65) Prior Publication Data

US 2005/0201657 A1 Sep. 15, 2005

Related U.S. Application Data

(63) Continuation of application No. 10/710,609, filed on Jul. 23, 2004, now Pat. No. 6,958,131, which is a continuation of application No. 10/065,152, filed on Sep. 22, 2002, now Pat. No. 6,787,110, which is a continuation of application No. 09/508,384, filed as application No. PCT/CH98/00389 on Sep. 10, 1998, now Pat. No. 6,455,004.

(30) Foreign Application Priority Data

Sep. 10, 1997 (CH) .................................. 2127/97

(51) Int. Cl.
*G01N 21/00* (2006.01)
*G02B 6/00* (2006.01)
*G02B 6/26* (2006.01)
*G02B 6/10* (2006.01)

(52) U.S. Cl. ............... 422/82.11; 422/82.05; 385/12; 385/37; 385/129; 385/130; 385/131; 385/132

(58) Field of Classification Search ............... None
See application file for complete search history.

(56) References Cited

U.S. PATENT DOCUMENTS 4,815,843 A 3/1989 Tiefenthaler et al.

(Continued)

FOREIGN PATENT DOCUMENTS

WO WO 95/03538 2/1995

OTHER PUBLICATIONS

Dubendorfer et al., Reference pads for miniature integrated optical sensors, Sensors and Actuators B, , pp. 116-121, vol. 38-39, Publisher: Elsevier Science S.A.

(Continued)

*Primary Examiner*—Jill Warden
*Assistant Examiner*—Neil Turk
(74) *Attorney, Agent, or Firm*—Oppedahl Patent Law Firm LLC

(57) ABSTRACT

The optical sensor contains an optical waveguide (1) with a substrate (104), waveguiding material (105), a cover medium (106) and a waveguide grating structure (101-103). By means of a light source (2), light can be emitted to the waveguide grating structure (101-103) from the substrate side and/or from the cover medium side. (101-103). With means of detection (11), at least two differing light proportions (7-10) radiated from the waveguide (1) can be detected. For carrying out a measurement, the waveguide can be immovably fixed relative to the light source (2) and the means of detection (11). The waveguide grating structure (101-103) itself consists of one or several waveguide grating structure units (101-103), which if so required can be equipped with (bio-)chemo-sensitive layers. The sensor permits the generation of absolute measuring signals.

6 Claims, 4 Drawing Sheets

U.S. PATENT DOCUMENTS

| | | | |
|---|---|---|---|
| 4,877,747 | A | 10/1989 | Stewart |
| 4,952,056 | A | 8/1990 | Tiefenthaler |
| 5,047,213 | A | 9/1991 | Finlan et al. |
| 5,071,248 | A | 12/1991 | Tiefenthaler et al. |
| 5,455,178 | A | 10/1995 | Fattinger |
| 5,479,260 | A | 12/1995 | Fattinger |
| 5,573,956 | A | 11/1996 | Hanning |
| 5,738,825 | A | 4/1998 | Rudigier et al. |
| 5,745,231 | A | 4/1998 | Groger et al. |
| 5,811,312 | A | 9/1998 | Hasegawa et al. |
| 5,815,278 | A * | 9/1998 | Johnston et al. ............. 356/445 |
| 5,822,472 | A | 10/1998 | Danielzik et al. |
| 5,846,842 | A | 12/1998 | Herron et al. |
| 6,127,183 | A | 10/2000 | Ivarsson et al. |
| 6,136,611 | A | 10/2000 | Saaski et al. |
| 6,395,558 | B1 | 5/2002 | Duveneck et al. |
| 6,455,004 | B1 | 9/2002 | Tiefenthaler |

OTHER PUBLICATIONS

Duberdorfer et al., Compact Integrated optical Immunosensor using replicated chirped grating coupler sensor chips, Applied Optics, , pp. 1890-1894, vol. 37, No. 10, Publisher: 1998 Optical Society of America.

Kunz et al., Replicated chirped waveguide gratings for optical sensing applications, Sensors and Actuators A, , pp. 482-486, vol. 46-47, Publisher: Elsevier Science S.A.

Lukosz et al., Output Grating Couplers on Planar Waveguides as integrated Optical Sensors, , vol. 11141, Publisher: 5th European Conference on Integrated Optics: ECIO '89.

R.E.Kunz, Totally integrated optical measuring sensors, Chemical, Biochemical, and Environmental Fiber Sensors III, 1991, pp. 98-113, vol. 1587.

R.E. Kunz, Miniature integrated optical modules for chemical and biochemical sensing, Sensors and Actuators, 1997, pp. 13-28, Publisher: Elsevier Science S.A.

\* cited by examiner

OPTICAL SENSOR AND OPTICAL PROCESS FOR THE CHARACTERIZATION OF A CHEMICAL AND/OR BIO-CHEMICAL SUBSTANCE

CROSS REFERENCE TO RELATED APPLICATIONS

This application claims priority from U.S. application Ser. No. 10/710,609 filed Jul. 23, 2004, which application claims priority from U.S. application Ser. No. 10/065,152 filed Sep. 22, 2002, now U.S. Pat. No. 6,787,110, issued Sep. 7, 2004, which is a continuation of U.S. application Ser. No. 09/508,384 filed Jun. 19, 2000, now U.S. Pat. No. 6,455,004, issued Sep. 24, 2002, which is the national stage of international application number PCT/CH98/00389, filed Sep. 10, 1998, which applications are each hereby incorporated herein by reference.

BACKGROUND OF INVENTION

The invention concerns an optical sensor and an optical process for the characterization of a chemical and/or bio-chemical substance.

Waveguide grating structures with and without a chemo-sensitive layer are described in the literature (refer to, e.g., EP 0 226 604 B1, EP 0 482 377 A2, PCT WO 95/03538, SPIE Vol. 1141, 192-200, PCT WO 97/09594, Advances in Biosensors 2 (1992), 261-289, U.S. Pat. No. 5,479,260, SPIE Vol. 2836, 221-234).

In EP 0 226 604 B1 and EP 0 482 377 A2, it is demonstrated, how the effective refractive index (resp., the coupling angle) of a chemo-sensitive grating coupler can be measured as a sensor signal. The sensor signal "effective refractive index" or "coupling angle" is a value which manifests a strong dependence on temperature.

Front-side in-coupling of light into a waveguide (refer to SPIE Vol. 1141, 192-200) is not practical, because a high positioning accuracy is required. In addition, the front side of the wave guide has to be of good optical quality. In PCT WO 95/03538 it is demonstrated how the absolute out-coupling angle of a mode is measured. This value, however, without referencing manifests a high dependence on temperature. In PCT WO 97/09594, chirped waveguide gratings are presented, which, however, also manifest a dependence on temperature.

In Advances in Biosensors 2 (1992), 261-289 it is shown how the disturbing "pore diffusion" can be referenced away with the three-layer waveguide model. The refractive index of the waveguiding film manifests drift, while the layer thickness of the waveguiding film (=sensor signal) remains stable. The layout is designed with movable mechanics, which does not permit rapid measurements. In addition, the sensor signal or the light emerging from the waveguide grating structure is recorded from the front side. Front side detection is unsuitable for a two-dimensional layout of waveguide grating structure units. Furthermore, the effective refractive indexes N(TE) and N(TM) for the two polarizations TE and TM are not simultaneously recorded, because for the recording of resonance coupling curves separated by angle a mechanical angular scan is carried out.

In U.S. Pat. No. 5,479,260, a bi-diffractive or multi-diffractive grating coupler is described, whereby the sensor signal is produced by the interferometry of two out-coupling beams of the same or of differing polarization (with the use of a polarizer). Interferometric measurements are complicated, because the intensities of the two beams have to be matched to one another. In addition, temperature fluctuations due to the interferometric signal generated by differing polarizations (using a polarizer) are only partially compensated.

In SPIE Vol. 2836, 221-234, a layout for a waveguide grating structure in connection with fluorescence or luminescence measurements is described. This layout, however, is not suitable for an (if necessary simultaneous) (absolute) temperature-compensated measurement on the basis of a direct detection. In addition, the waveguide grating structure is mounted on a revolving table.

In Applied Optics 20 (1981), 2280-2283, a temperature-independent optical waveguide is described, whereby the substrate is made of silicon. Silicon is absorbent in the visual spectral range. In the case of chemo-sensitive waveguide grating structures, however, the in-coupling takes place in preference from the substrate side. In addition, Applied Optics 20 (1981), 2280-2283, grating couplers which are not temperature-independent are described.

SUMMARY OF INVENTION

The invention presented here has the object of creating a (bio-)chemo-sensitive optical sensor and to indicate an optical process for the characterization of a (bio-)chemical substance, which do not have the above disadvantages. With the invention, in particular:

(1) sensor signals can be generated, which manifest a low dependence on temperature and/or a low dependence on the diffusion of the specimen liquid into the micropores of a waveguiding film;

(2) both the measurement of (absolute) sensor signals with respect to a direct detection (absolute out-coupling angles $\alpha(TE)$ and $\alpha(TM)$ for the TE- or TM-wave, effective refractive indexes $N(TE)$ and $N(TM)$ for the TE- or TM-wave, layer thickness $t_F$ of the waveguiding film etc.) as well as the measurement of (absolute) sensor signals with respect to a marking detection (referenced fluorescence-, luminescence-, phosphorescence signals, etc.), are possible; and (3) sensor signals remain stable with respect to a slight tilting and/or displacement of the waveguide grating structure, because (local and angular) differences of sensor signals or referenced sensor signals are measured.

The optical sensor according to the invention contains at least one optical waveguide with a substrate, waveguiding material, a cover medium and at least one waveguide grating structure, at least one light source, by means of which light can be emitted from the substrate side and/or from the cover medium side onto at least a part of the waveguide grating structure, and means for the detection of at least two differing light proportions, whereby with at least one detection agent light emitted into the substrate and/or cover medium can be detected, whereby for the carrying out of a measurement the waveguide can be fixed immovably with respect to the at least one light source and the means of detection.

In the case of the optical process according to the invention for the characterization of a chemical and/or bio-chemical substance in a specimen by means of an optical waveguide containing at least one waveguide grating structure, the specimen is brought into contact with the waveguide in at least one contact zone, in the waveguide in the region of the at least one contact zone at least one light wave is excited through the waveguide grating structure, the at least one light wave is brought into interaction with the specimen, light in at least two differing proportions is detected, of which at least one proportion originates from the region of the contact zone, and at least one absolute measuring signal is generated by the evaluation of the detected light.

The waveguide grating structure consists of one or several waveguide grating structure units, which are arranged one-dimensionally or two-dimensionally (e.g., in a matrix shape or circular shape).

A possible xy displacement (or only an x-displacement) of the reading head (the reading heads) from one waveguide grating structure to the other or a possible xy-displacement (or only x-displacement) of the waveguide grating structure can quite well be applied.

A waveguide grating structure unit consists of at least two "sensing pads" (sensor platforms, sensor paths), which differ from one another in at least one of the following characteristics:

(a) The light waves guided in the "sensing pads" differ in their polarization (TE-wave or TM-wave), whereby the generated sensor signal is not produced by interferometric measurement.
 (b) The light waves guided in the "sensing pads" differ in their mode number.
 (c) The two chemo-sensitive layers assigned to the "sensing pads" manifest a differing specificity (ligand 1 selectively binds (inside or on the surface) to the chemo-sensitive layer covering the "sensing pad 1"; ligand 2 selectively binds (inside or on the surface) to the chemo-sensitive layer covering the "sensing pad 2").
 (d) The chemo-sensitive layer assigned to the first "sensing pad" manifests specificity for one ligand (with or without "non-specific binding"), while the (chemo-sensitive) layer assigned to the second "sensing pad" manifests no specificity (with or without "non-specific binding") (example: Dextran layer, to which no identification molecule (e.g., an antibody) is bound).
 (e) The light waves guided in the "sensing pads" differ in their wavelength.

A "sensing pad", in which guided light waves of differing polriztion (TEwave or TM-wave) are excited, counts as two "sensing pads" (difference in the polarization!), providing the sensor signal generated is not produced by interferometric measurement.

A "sensing pad", in which guided light waves of differing mode number are excited, counts as two "sensing pads" (difference in the mode number!).

A "sensing pad", in which guided light waves of differing wavelengths are excited, counts as two "sensing pads" (difference in the wavelength!).

The first and second "sensing pad" can also be considered as signal and reference path. The two "sensing pads" can (but do not have to) have the same structure.

The (bio-)chemo-sensitive contacts the waveguiding film in a contact zone. This contact zone normally in the case of the direct detection contains at least one grating. (In the case of interferometric measurements with the same polarization, for a direct detection the (bio-)chemo-sensitive layer can also only be located between two gratings (also refer to EP 0 226 604)). (In the case of interferometric measurements with two differing polarizations (using a polarizer), the (bio-)chemo-sensitive layer can also be located on a multi-diffractive (bi-diffractive) grating (refer to U.S. Pat. No. 5,479,260)).

On principle, for example, the value S (signal path) cS (reference path) can serve as a possible referenced sensor signal, whereby S (signal path) and S (reference path) are the sensor signals in the first "sensing pad" (signal path) or in the second "sensing pad" (reference path) and c is a calibration factor. In the case of the same polarization, sensibly c=1. In the case of different polarizations, with c the differing sensitivities of the two polarizations can be taken into account. In the case of different wavelengths or mode numbers, with c the differing sensitivities of the wavelengths or of the mode numbers can be taken into account. Advantageously, signal path and reference path are as close together as possible.

The referenced sensor signal in the case of the same polarization furthermore has the advantage that disturbances δ, such as, e.g., those caused by temperature fluctuation, light wavelength fluctuation, undesired diffusion of molecules in the waveguides, resp. in the chemo-sensitive layer, unspecific bindings, fluctuations of the concentration of the molecules not to be detected, etc., or combinations of these, can be referenced away, i.e., the referenced sensor signal is independent of δ, because S (signal path)+δ−(S (reference path)+δ)=S (signal path)−S (reference path).

In preference, mono-mode waveguides are utilized, which only carry the fundamental TE-mode or only the fundamental TE-mode and the fundamental TM-mode. The waveguiding film should preferably consist of a high-refractive material, which guarantees the generation of high sensitivities. The waveguiding film can be coated with a chemo-sensitive layer (e.g., an anti-body layer (e.g., suitable for the detection of a corresponding antigen), a dextran layer with identification molecule (e.g., anti-bodies), receptors, DNA-sections, a silicon layer for the detection of hydrocarbons, etc.). The waveguiding film itself, however, can also represent a chemo-sensitive layer. Rib waveguides can also be utilized.

A "sensing pad" comprises at least one grating, but can also comprise a (possibly more strongly modulated) in-coupling grating and at least one out-coupling grating. The grating periods of in-coupling grating and out-coupling grating can be different (and are in most cases different).

In-coupling grating and out-coupling grating can be uni-diffractive or multi-diffractive grating structures (bi-diffractive gratings, gratings with changing grating period and/or with changing grating diffraction vector, etc.).

A preferred "sensing pad" arrangement consists of three gratings, whereby the middle grating represents the in-coupling grating and the two outer gratings two out-coupling gratings. With a strongly modulated in-coupling grating, for example, one succeeds in exciting modes in forward and reverse direction with a sole (resp., with two) incident (if so required slightly focussed) light beam(s). While a slight displacement of the incident light beam in the mode propagation direction or a slight tilting of the waveguide grating structure with respect to the incident light beam (in the plane of incidence) change the intensity of the modes (running in forward and/or reverse direction) as a result of the changed coupling geometry, not, however, the out-coupling angle(s) or the difference of the out-coupling angles (=double absolute out-coupling angle), which represent possible sensor signals.

DETAILED DESCRIPTION

A further preferred "sensing pad" arrangement also consists of three gratings, whereby the two outer gratings form (possibly more strongly modulated) in-coupling gratings and the middle grating the out-coupling grating.

Figure 1:
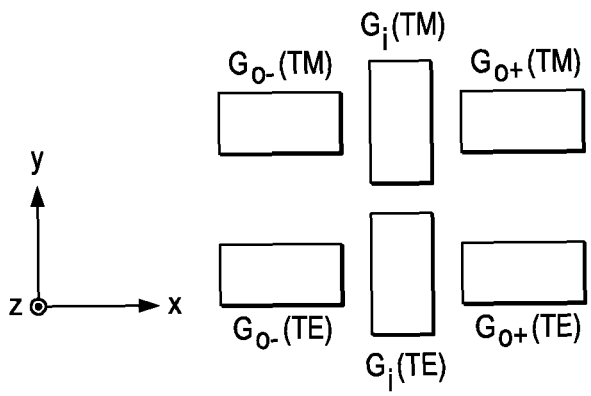
FIG. 1 shows the above preferred "sensing pad" arrangement both for the TE-mode as well as for the TM-mode, whereby the two "sensing pads"are located adjacent to one another.

In case of the detection of (bio-)molecular interactions with the arrangement according to FIG. 1 (or equivalent arrangements), the waveguide structure unit is coated with a (bio-)chemo-sensitive layer, to which then in the experiment a specific binding partner binds, which leads to a change of the out-coupling angles $\alpha(TE)=(\alpha(TE+)-\alpha(TE-))/2$ and $\alpha(TM)=(\alpha(TM+)-\alpha(TM-))/2$ (notation: e.g., $\alpha(TE+)$: out-coupling angle of the TEmode running in +xdirection or to a change of the effective refractive indexes N(TE) and N(TM) and of the integrated optical values derivable from it such as, e.g., of the layer thickness $t_F$ of the waveguiding film in the three-layer waveguide model (see further below). Different waveguide grating structure units can be coated with different chemo-sensitive layers.

The out-coupling angle of the two out-coupling gratings (resp., of the out-coupling grating) of the preferred "sensing pad" arrangement enable an absolute determination of the out-coupling angle (resp., of the effective refractive index), although the out-coupling of the two light beams does not take place at one and the same location.

In case of two adjacent "sensing pads" for the TE- and the TM-mode according to the preferred "sensing pad" arrangement (see FIG. 1), the out-coupling even takes place at four different locations.

The "sensing pad" for the TE-mode enables the determination of the effective refractive index N(TE) of the TE-mode. The "sensing pad" for the TM-mode enables the determination of the effective refractive index N(TM) of the TM-mode. In case of simultaneous illumination of the two "sensing pads" (with, e.g., a single light field with 45° linear polarized light or circular (or elliptical) polarized light), the determination of the out-coupling angle (of the effective refractive index) for the TE- and TM-mode can take place simultaneously.

FIG. 1 illustrates an advantageous embodiment of a waveguide grating structure unit. The "sensing pad" for the TE-mode consists of an in-coupling grating $G_i(TE)$ and the two out-coupling gratings $G_{o+}(TE)$ und $G_{o-}(TE)$ located on the left and right of the in-coupling grating. The sensing pad for the TM-mode consists of the in-coupling grating $G_i(TM)$ and the two out-coupling gratings $G_{o+}(TM)$ and $G_{o-}(TM)$ located on the left and right of the in-coupling grating and it is located adjacent to the "sensing pad" for the TE-mode. In order to keep the influence of disturbances (e.g., temperature fluctuations) low, the two "sensing pads" should be located as closely as possible adjacent to one another. The grating lines are aligned parallel to the yaxis.

It is advantageous if the out-coupling gratings $G_{o+}(TE)$, $G_{o-}(TE)$, $G_{o+}(TM)$, $G_{o-}(TM)$ are completely illuminated by the guided light waves, as a result of which it is ensured that in case of the respective out-coupling grating the sensor surface corresponds to the surface of the out-coupling grating. This is achieved by selecting (a) the width of the out-coupling grating in y-direction smaller than/equal to the width of the in-coupling grating in y-direction and (b) the illumination spot on the in-coupling grating having a y-width, which is greater than/equal to the y-width of the out-coupling gratings, and the illumination spot including the complete y-width of an out-coupling grating.

An advantageous embodiment is the one, in the case of which the two in-coupling gratings $G_i(TE)$ and $G_i(TM)$ are simultaneously illuminated with one (or two (wedge-shaped) light field(s) linear polarized under 45°. With this, simultaneously the TE-mode and the TM-mode (in the forward and reverse direction) can be excited and simultaneously all (in the case presented here: four) out-coupling angles can be measured. $G_i(TE)$ and $G_i(TM)$ in preference have differing grating periods.

It is, however, also possible that a "sensing pad" as such carries out the function of a "sensing pad" for the TE-mode and the function of a "sensing pad" for the TM-mode. The second "sensing pad" (located adjacent to it) is then either not present or else is utilized as a check or reference. (This reference "sensing pad" can, e.g., be coated with a second chemo-sensitive layer or with a non-specific layer, i.e., a layer which has no specificity (with or without "non-specific binding"). If the in-coupling grating of a "sensing pad" is illuminated with TE-light as well as with TM-light under the corresponding in-coupling angles (e.g., with 45° (linear polarized light), then in the one "sensing pad" both the TE-mode as well as the TM-mode are excited (if so required both in forward as well as in reverse direction).

It is also possible to excite the TE-mode only in forward direction and the TM-mode only in reverse direction (or vice-versa) or the TE-mode and the TM-mode only in forward direction (or vice-versa). In such a case, then the corresponding two out-coupling angles or their difference are measured.

Utilized as detectors are advantageously one- or two-dimensional (digital or analogue) position-sensitive detectors (PSD), photo-diode arrays, CCD line- or surface camera(s), etc. The out-coupled light beams are advantageously focussed with a lens, whereby the focus does not indispensably have to be situated exactly on the detector surface. The out-coupling gratings can also be focusing gratings. This has the benefit that the lens-effect is already integrated in the out-coupling grating.

It is also possible to select the direction of the grating lines of the out-coupling grating in such a manner, that the grating lines are vertical to the propagation direction of the mode. Advantageously, the tilting of the grating lines (resp., of the grating diffraction vectors) of the out-coupling gratings of two adjacent "sensing pads" has an inverse operational sign. With this, a better separation of the out-coupled light waves can be achieved.

The in-coupling grating can also be selected in such a manner, that the grating period in xdirection or ydirection does not remain constant or is graduated. The requirements of the accuracy of the setting of the angle of incidence are relaxed as a result of this.

The in-coupling gratings shown in FIG. 1 in preference have a strong modulation and are characterized by a short width in x-direction. As a result, the requirements of the accuracy of the setting of the angle of incidence are relaxed, because the light can now in-couple from a greater angle segment.

Figure 2A:
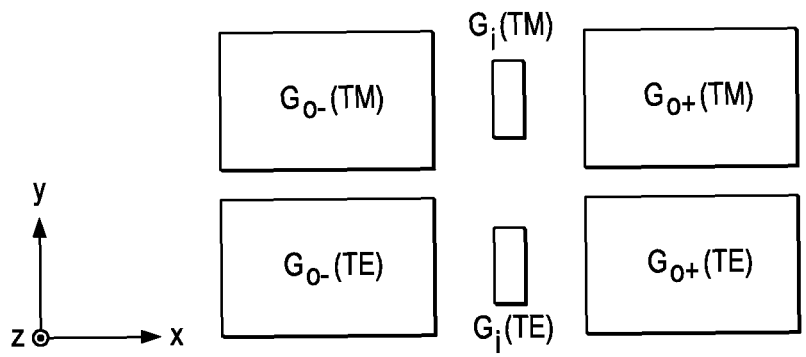
FIG. 2 illustrates further waveguide grating structure units.
Figure 2B:
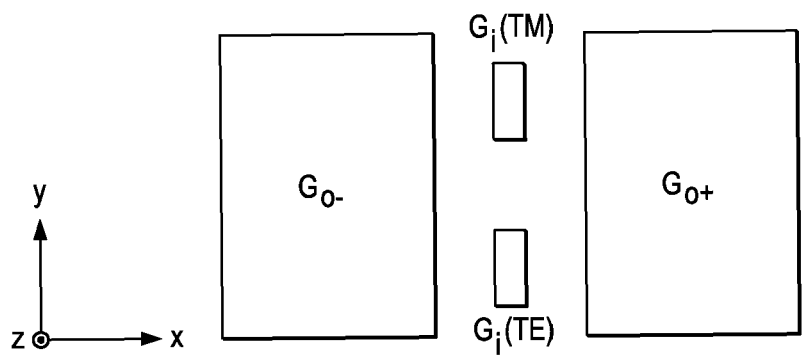

FIGS. 2(a) and 2(b) illustrate two further embodiments of waveguide grating structures, whereby here the dimension of the in-coupling gratings in ydirection is smaller than that of the out-coupling gratings. In FIG. 2(b), a uniform out-coupling grating $G_{O-}$ for the TE- and TM-wave running in (-x) direction and a uniform out-coupling grating $G_{O+}$ for the TE- and TM-wave running in (+x) direction are depicted.

Figure 3:
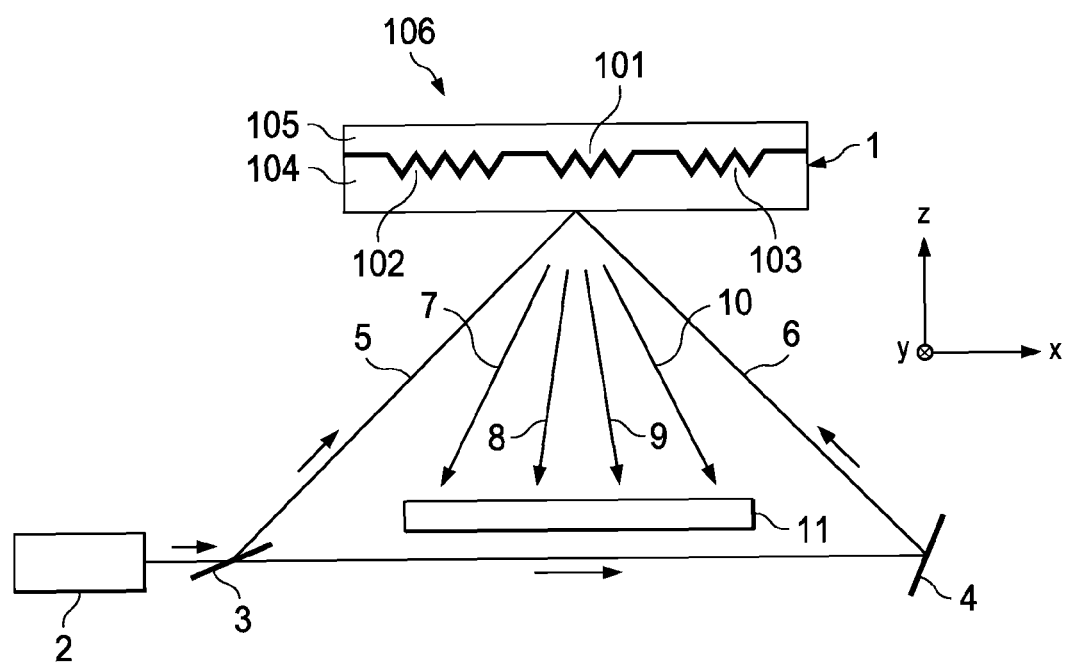
FIGS. 3-5 show an optical sensor according to different embodiments of the invention.

FIG. 3 illustrates an embodiment of a sensor according to the invention. The sensor contains a waveguide 1 with a substrate 104, a waveguiding material 105 and a cover medium 106 as well as with a waveguide grating structure according to FIG. 1. A light source 2 generates, for example, 45° linearly polarized light; for this purpose, a linearly polarized laser with a polarization plane inclined to the drawing plane by 45° can be utilized. Through a beam splitter 3 or a mirror 4, two impinging light beams 5, 6 are produced. The light beams 5, 6 impinge on the two in-coupling gratings 101

(of which in the side view of FIG. 3 only one is visible) of the two "sensing pads" through the substrate 104 and in the first "sensing pad" generate a TMwave in forward and reverse direction. The light waves are out-coupled through four out-coupling gratings 102, 103 (of which in the side view of FIG. 3 only two are visible) from the waveguide grating structure and radiated into the substrate 104. After passing through the substrate 104 they spread as light fields 7-10 and impinge on a two-dimensional CCD-detector 11. If so required, there can be a lens system (not illustrated) between the waveguide 1 and the detector 11.

Figure 4A:
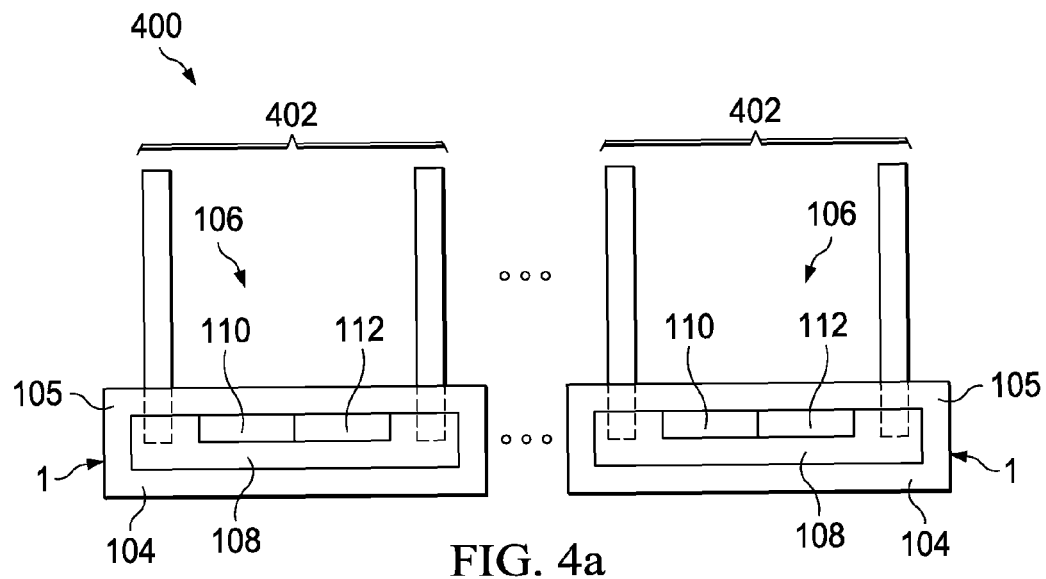
Figure 4B:
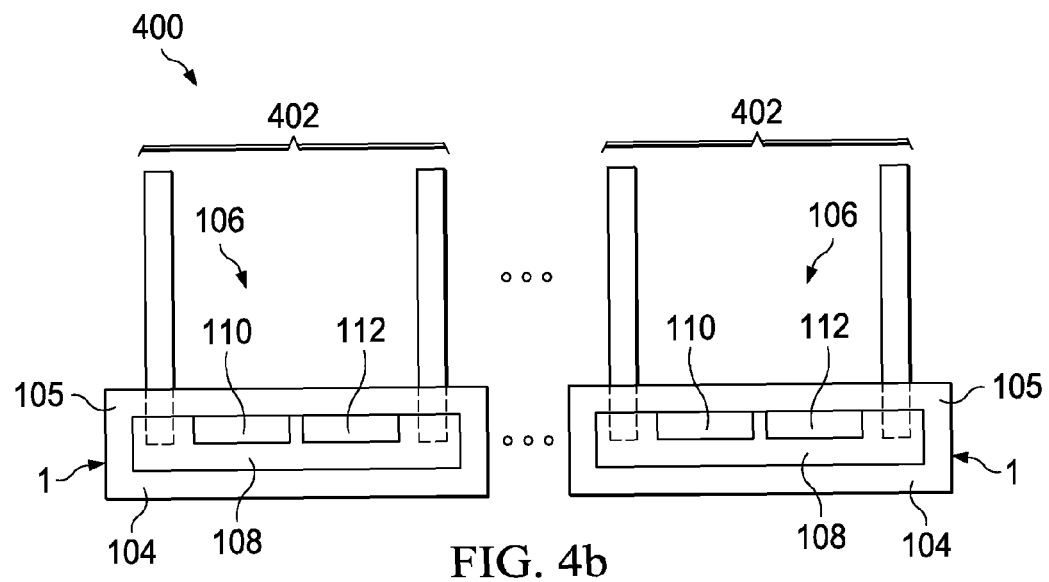

FIG. 4a illustrates an embodiment of a sensor 400 which contains an optical waveguide 1 that includes a substrate 104, a waveguiding material 105 and a cover medium 106 as well as at least one waveguide grating structure 108, where each waveguide grating structure 108 includes a sensing pad 110 and a reference sensing pad 112, and where a well 402 or a matrix of wells 402 is arranged on the at least one waveguide grating structure 108 or in the at least one waveguide grating structure 108. FIG. 4b illustrates the sensor 400 where the sensing pad 110 and reference sensing pad 112 are arranged a distance from one another.

Figure 5A:
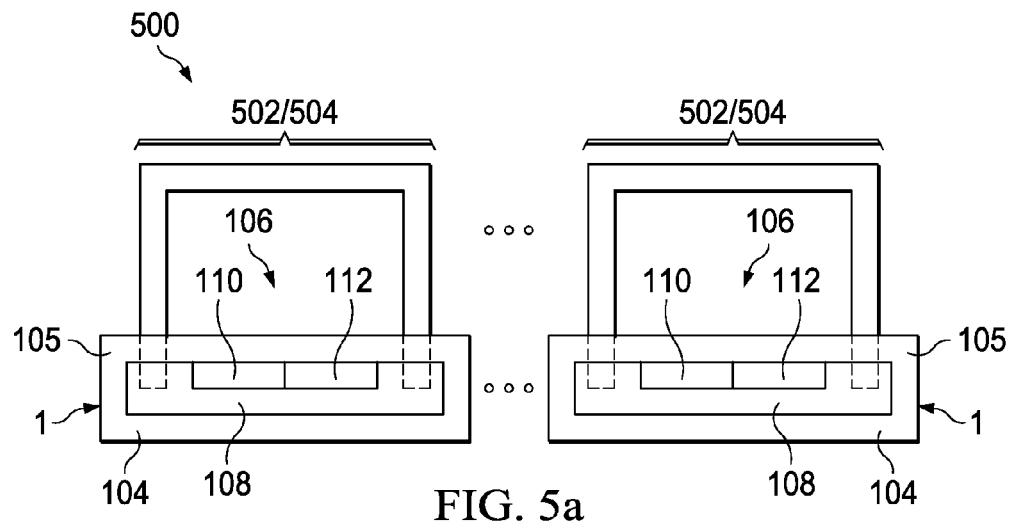
Figure 5B:
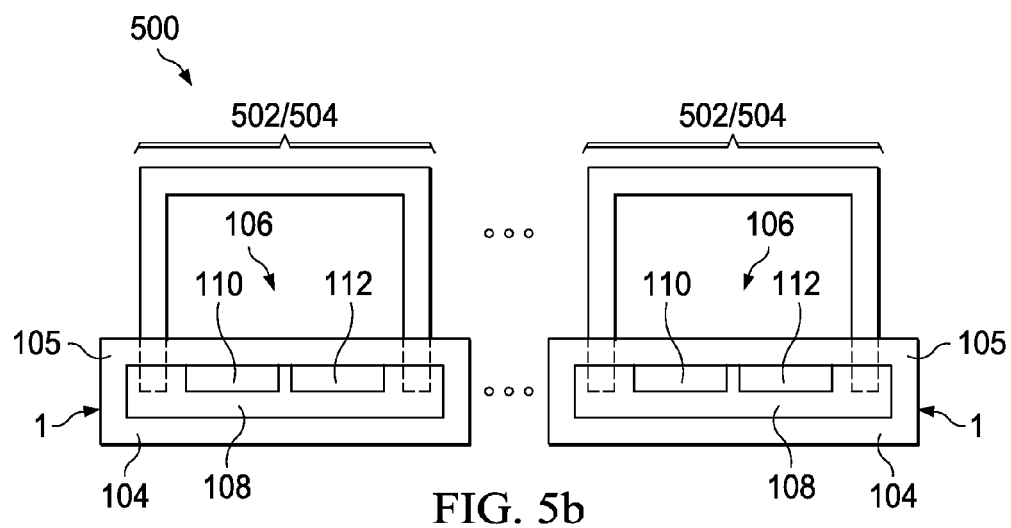

FIG. 5a illustrates an embodiment of a sensor 500 which contains an optical waveguide 1 that includes a substrate 104, a waveguiding material 105 and a cover medium 106 as well as at least one waveguide grating structure 108, where each waveguide grating structure 108 includes a sensing pad 110 and a reference sensing pad 112, and where a flow-through cell 502 or a matrix of flow through cells 502 or a capillary vessel 504 or a matrix of capillary vessels 504 is arranged on the at least one waveguide grating structure 108 or in the at least one waveguide grating structure 108. FIG. 5b illustrates the sensor 500 where the sensing pad 110 and reference sensing pad 112 are arranged a distance from one another.

If in the two "sensing pads" one operates with differing polarization and with a chemo-sensitive layer assigned to the waveguide grating structure, then, for example, the sensor signal $S=t_F$ (=layer thickness of the waveguiding film in the three-layer waveguide model) can be generated (also see further below). If now a second waveguide grating structure unit, which also permits the generation of the sensor signal $S=t_F$, is laid next to the first waveguide grating structure unit (now to be considered as a whole as signal path) and the second waveguide grating structure unit (now to be considered as a whole as reference path) coated with, for example, a chemo-sensitive layer of differing specificity or with a non-specific chemo-sensitive layer with or without "non-specific binding" (e.g., a dextran layer, to which no identification molecule is bound), then, for example, the value $t_F$ (measured in the signal path)$-t_F$(measured in the reference path) can serve as sensor signal.

Athough the effective refractive indexes N(TE) and N(TM) of the TE- or TM-mode are possibly not measured at the same point (the two "sensing pads" are, however, in the case of a chemo-sensitive sensor coated with the same chemo-sensitive layer), with the waveguide grating structure unit the interesting sensor signals S and/or $\Delta$S with $$\Delta S = \Delta\alpha(TM) - \Delta\alpha(TE) = \Delta(\alpha(TM) - \alpha(TE))\ (\Delta S = \Delta(\alpha(TE) - \alpha(TM)))$$

($\alpha$=out-coupling angle)

$$\Delta S = \Delta N(TM) - \Delta N(TE)\ (\Delta S = \Delta N(TE) - \Delta N(TM)),$$

whereby the layer thickness of the waveguiding film in preference should be selected in such a manner, that for the sensitivity of the refractive index of the cover medium $\partial N(TE)/\partial n_C = \partial N(TM)/\partial n_C$ is applicable, which at least eliminates the influence the refractive-index changes of the cover medium on the sensor signal have on the sensor signal (the refractive index $n_C$ of the cover medium depends on the temperature, i.e., $n_C = n_C(T)$, whereby T is the temperature), $$\Delta S = \Delta t_F = \text{const}((\partial N(TE)/\partial T)^{-1}\Delta N(TE) - (\partial N(TM)/\partial T)^{-1}\Delta N(TM))$$

whereby const=$((\partial N(TE)/\partial T)^{-1}(\partial N(TE)/\partial t_F) - (\partial N(TM)/\partial T)^{-1}(\partial N(TM)/\partial t_F))^{-1}$ and the change of the layer thickness $\Delta t_F$ is calculated from the system of equations $$\Delta N(TE) = (\partial N(TE)/\partial t_F)\Delta t_F + (\partial N(TE)/\partial T)\Delta T \quad \text{(equation 1)}$$

$$\Delta N(TM) = (\partial N(TM)/\partial t_F)\Delta t_F + (\partial N(TM)/\partial T)\Delta T$$

and $\partial N/\partial T$ is the temperature coefficient of the waveguide complete with cover (=specimen) for the corresponding mode ($\partial N/\partial T$ is calculated taking into account the temperature coefficient $(dN/dT)_{GRATING}$ of the grating experimentally (or according to theory) (also see further below)), $\Delta S = \Delta t_F$, whereby the layer thickness $t_F$ is calculated with the three-layer waveguide model (with N(TE) and/or N(TM) as input parameter), $\Delta S = \Delta t_A$, whereby the change of the additional layer thickness $\Delta t_A$ is calculated from the system of equations $$\Delta N(TE) = (\partial N(TE)/\partial t_A)\Delta t_A + (\partial N(TE)/\partial T)\Delta T \quad \text{(equation 2)}$$

$$\Delta N(TM) = (\partial N(TM)/\partial t_A)\Delta t_A + (\partial N(TM)/\partial T)\Delta T,$$

$\Delta S = \Delta t_A$, whereby the additional layer thickness $t_A$ is calculated with the four-layer waveguide model (resp., five-layer waveguide model), $\Delta S = \Delta\Gamma$, whereby the mass density by surface $\Gamma$ (refer to Chem. Commun. 1997, 1683-1684) is calculated with the four-layer waveguide model (or also with the three-layer waveguide model with the utilization of approximations (refer to J. Opt. Soc. Am. B, Vol. 6, No. 2, 209-220), etc., are measured. The above sensor signals are interesting, because they manifest a low dependence on temperature. On principle, however, during the measurement it still has to be taken into account that also the grating period manifests a temperature-dependence as a result of the thermal expansion coefficient of the sensor chip. Applicable is $\Delta\Lambda = \alpha\Lambda\Delta T$, whereby $\Delta\Lambda$ is the change of the grating period $\Lambda$, $\Delta T$ the change of the temperature T and $\alpha$ the thermal expansion coefficient (typically 4.5 $10^{-6}$ K$^{-1}$ for glass and 6.1 $10^{-5}$ K$^{-1}$ for polycarbonate). The $(dN/dT)_{GRATING} = I(\lambda/\Lambda)\alpha$ caused by the grating, whereby I is the order of diffraction and $\lambda$ the wavelength, contributes to the temperature coefficient $(dN/dT)_{CHIP}$(=experimental measured value) of the complete sensor chip as follows: $(dN/dT)_{CHIP} = (dN/dT)_{WAVEGUIDE+SPECIMEN} + (dN/dT)_{GRATING}$, whereby $(dN/dT)_{WAVEGUIDE+SPECIMEN}$ is the temperature coefficient of the waveguide complete with cover (=specimen).

The sensor signals S and $\Delta$S can be recorded in function of the time. One can, however, also only measure and compare an initial and a final condition on a waveguide grating structure unit, whereby, for example, in the interim other waveguide grating structure units can be evaluated or the even the waveguide grating structure can be removed from the measuring unit in the meantime, because absolute angles or differences of angles (resp., distances (differences of distances) of light points) are measured and these values remain stable with respect to a tilting or displacement. The determination of a measured value can be carried out by means of an individual measurement, also, however, by means of a statistical evaluation (e.g., averaging) of several individual measurements.

If apart from temperature changes $\Delta T$, other interferences are also present, such as, e.g., diffusion of the specimen liquid into the micro-pores of a porous waveguiding film (which leads to a change in the refraction index $\Delta n_F$ of the waveguiding film) or tensions (such as, e.g., compressive strain or tensile stress) or changes in stress are present or if in general only pore diffusion is present, then (in the first case under certain conditions (e.g., the course in function of time of the pore diffusion with the temperature T as group of curves parameter is known) (approximately), then a (common) interference value $\xi$ with $N(t_F,\xi)=N(t_F, n_F(\xi), n_S(\xi), n_C(\xi))$ or $N(t_A, \xi)=N (t_F, t_A, n_A(\xi), n_F(\xi), n_S(\xi), n_C(\xi))$ can be introduced. Equation (1) or (2) then take on the form $$\Delta N(TE)=(\partial N(TE)/\partial S)\Delta S+(\partial N(TE)/\partial\xi)\Delta\xi \qquad \text{(equation 3)}$$

$$\Delta N(TM)=(\partial N(TM)/\partial S)\Delta S+(\partial N(TM)/\partial\xi)\Delta\xi,$$

whereby $\Delta S$ is the sensor signal $\Delta t_F$ (or $\Delta t_A$) and, for example, in the case of the three-layer waveguide model $\partial N/\partial\xi=(\partial N/\partial n_F)(\partial n_F/\partial\xi)+(\partial N/\partial n_S)(\partial n_S/\partial\xi)+(\partial N/\partial n_C)(\partial n_C/\partial\xi)(+(\partial N/\partial t_F)(\partial t_F/\partial\xi))$, providing $t_F$ is $=t_F(\xi)$). Logically directly from $\xi=T$ formula (1) or formula (2) follows. $\xi=n_F$, describes, e.g., the diffusion at a constant temperature.

Also in the case of the presence of several interferences, it is possible to operate with the three-layer waveguide model and the modes equation solved (example: input: $N(TE)$, $N(TM)$, output: $t_F$, $n_F$(=refractive index of the waveguiding film) or $t_F$, $n_C$(=refractive index of the cover medium) or $t_F$, $n_S$(=refractive index of the substrate)). In the three-layer waveguide model, waveguiding film, chemo-sensitive layer and specific binding partner are considered as being a layer with one refractive index. Although $n_F$ and $n_C$ (and if applicable $n_S$) are not precisely known and if applicable change during the experiment on the basis of an interference, the measured value $t_F$ is relatively independent of the interference, dependent on the contrary, however, on the binding process. The interference is so-to-say packed into the second output value, the parameter "refractive index".

Fundamentally, pore diffusion and temperature fluctuations are independent manifestations and should be described by two interference values $\xi_1$ and $\xi_2$ (generalization: k independent disturbances are described by k independent disturbance values $\xi_1, \ldots, \xi_k$). From $N(t_F, \xi_1, \ldots, \xi_k)$ for both polarizations, for a given mode number and for a given wavelength follows $$\Delta N=(\partial N/\partial t_F)\Delta t_F+(\partial N/\partial\xi_1)\Delta\xi_1+\ldots+(\partial N/\partial\xi_k)\Delta\xi_k. \qquad (4)$$

Because the disturbance values can influence the waveguide parameters $t_F$, $n_F$, $n_S$, $n_C$, the following is applicable:

$$\partial N/\partial\xi_i=(\partial N/\partial t_F)(\partial t_F/\partial\xi_i)+(\partial N/\partial n_F)(\partial n_F/\partial\xi_i)+(\partial N/\Delta n_s)(\partial n_S/\partial\xi_i)+\partial N/\partial n_C)(\partial n_C/\partial\xi_i) \qquad \text{(equation 5)}$$

($1\leq i\leq k$) (the analogue is also applicable for $N(t_A, \xi_1, \ldots, \xi_k)$). For the pore diffusion ($\xi_1=n_F$) and the temperature change ($\xi_2=T$) from Eq. (4) results $$\Delta N=(\partial N/\partial t_F)\Delta t_F+(\partial N/\partial n_F)\Delta n_F+(\partial N/\partial T)\Delta T \qquad \text{(equation 6)}$$

for both polarizations, a given mode number and a given wavelength. $\partial N/\partial T$ can, e.g., be determined experimentally. If, e.g., both polarizations are measured, then (6) represents two equations with three unknown values. If, however, measurements are carried out at several wavelengths (taking into account the refractive index dispersions) and/or mode numbers, then several systems of equations respectively consisting of three equations and three unknown values can be put together and solved. If the dispersion in $\Delta n_F(\lambda)$ is taken into account as an unknown value ($\lambda$=wavelength), then one obtains, e.g., with two wavelengths $\lambda_1$ and $\lambda_2$ and two polarizations four equations with four unknown values $\Delta t_F$, $\Delta n_F(\lambda_1)$, $\Delta n_F(\lambda_2)$, $\Delta T$ and from them determines the unknown values. The value $\Delta t_F$ forms the sensor signal.

In analogy to further above, however, also the sensor signal $t_F$ and the disturbance values from the (three-layer- or four-layer-) mode equations for the two polarizations and for several wavelengths and mode numbers can be determined, this under the prerequisite, that the system of equations can be numerically solved.

Fundamentally also the layer thicknesses are to a certain degree dependent on the temperature (also refer to Applied Optics 20 (1981), 2280-2283), which fact, however, has been neglected in the formulas (1), (2) and (3) in the approximation. It is, however, also possible with respect to at least one specimen select such a combination of (several) layers and substrate, that the temperature coefficient of the waveguide or of the grating coupler (resp., of the waveguide grating structure) with respect to at least one sensor signal S (=$\alpha$(TE), $\alpha$(TM), $\alpha$(TM)–$\alpha$(TE), N(TE), N(TM), N(TM)–N(TE), $t_F$, $t_A$ etc.) is practically zero (the sensitivity, however, still remains high). In this, e.g., one of the layers involved can be an $SiO_2$ layer.

The absolute temperature coefficient with respect to a sensor signal S is dS/dT, the corresponding relative temperature coefficient is $(1/S)(dS/dT)$. with $dN(TE)/dT=0$ or $dN(TM)/dT=0$, also $S=N(TE)$ or $S=N(TM)$ become interesting sensor signals independent of the temperature.

If in a "sensing pad" only one grating is present, then, for example, with the reflection arrangement described in the European patent application 0 482 377 A2 (possibly with a sensor chip with tilting of the grating plane versus the lower substrate plane) measurements are possible. The measurement with the reflection arrangement on weakly or more strongly modulated (mono-diffractive or multi-diffractive) waveguide gratings (homogeneous gratings, superimposed gratings with different grating periods and/or grating orientations, chirped gratings, etc.) can be carried out both for TE- as well as for TM-waves. The mode excitation can take place from the left, the readout from the right or vice-versa. For example, in a "sensing pad" the excitation of the TE-wave can take place from the left and the excitation of the TM-wave from the right. In a second "sensing pad" (possibly with a different grating period and/or grating orientation) the excitation can be in reverse to the first "sensing pad". The readout can take place in the reflected and transmitted light field in the zero-th or higher diffraction order. With this, it is also possible to determine absolute coupling angles with the reflection arrangement. The measured absolute coupling angle, which in essence in case of the same grating period (and the same diffraction order) corresponds to half of the angle difference between the two corresponding resonance minimums, does not change, even if the sensor chip is slightly tilted. From the absolute coupling angles for the TE-wave or the TM-wave, the corresponding effective refractive indexes and further integrated optical measured values can be determined, such as, e.g., the layer thickness $d_F$ of the waveguiding film in the three-layer waveguide mode, etc.

It is of course also possible that in the first "sensing pad" the excitation of the TE- and TM-wave takes place from the left and the readout from the right (if so required with only one CCD) and in the second "sensing pad" (possibly with a differing grating period) in reverse.

It is also possible that the plane of incidence of the beam guidance responsible for the reference path (second "sensing pad") is rotated or tilted or rotated and tilted versus the plane of incidence of the beam guidance responsible for the signal path (first "sensing pad"). First and second "sensing pads" can also coincide. The coupling angles for the TE-wave and the TM-wave can also be measured at different wavelengths and/or mode numbers.

A further "sensing pad" arrangement consists of two (identical) chirped gratings (gratings with graduated grating period), whereby one grating serves as in-coupling grating and one grating as out-coupling grating. Chirped gratings are known from the literature (refer to, e.g., the patent application WO 97/09594). The signal "sensing pad" and the reference "sensing-pad" can have the same or also an opposing chirp direction (direction, in which the grating period changes (e.g., becomes bigger), it is vertical to the direction of the mode propagation). The "sensing pads" can be coated with the same (bio-)chemo-sensitive layer (see below) or else have differing ((biolayers, whereby the ((bio-)chemo-sensitive) layer of the second "sensing pad" (reference "sensing pad") is a different (bio-)chemo-sensitive layer or a non-specific ((bio-)chemo-sensitive) layer with or without "non-specific binding" (e.g., dextran without identification molecule) or else a purely protective layer.

The chirped grating, which is responsible for the in-coupling, is illuminated with a (not wedge-shaped or if so applicable (slightly) wedge-shaped) light strip, of which a certain proportion, in the case of which the in-coupling conditions are fulfilled, is in-coupled to the waveguide. It is also possible to simultaneously illuminate the in-coupling chirped gratings of the signal—"sensing pad" and reference—"sensing pad" (if so required with a single, longer light strip) (if so required with 45° linear polarized or circular (or elliptically) polarized light (for the excitation of modes of both polarizations)). In the case of a excitation of modes of differing polarization under a fixed angle of incidence, the corresponding grating periods of the two "sensing pads" are different.

In the case of the same polarization and opposite chirp direction of signal "sensing pad" and reference "sensing pad" (both "sensing pads" are coated with the same (biolayer), the two out-coupled light spots on the basis of the (biobinding travel (practically) vertical to the direction of propagation of the modes towards one another or away form one another (depending on the chirp direction or the chirp orientation). The position of the light spots is measured with PSDs or with a one- (or two-) dimensional CCD. Through the change of the distance of the two light spots, the change of the effective refractive index of the corresponding polarization can be calculated. The distance of the two light spots is an absolute value, because the distance of the two light spots is independent of displacements or of small tilting. (If the signal and reference paths have a differing polarization, then the measuring signal $\Delta N(TM)-\Delta N(TE)$ can be determined.) In the case of the same polarizations, same chirp directions of the two "sensing pads", but differing (bio-)chemo-sensitive layer (e.g., on the signal path a specific layer, on the reference path a non-specific layer), the distance of the two light spots forms a referenced (absolute) sensor signal.

The arrangement described in the paragraph before the last one can once again be duplicated for the other polarization (with an adaptation of the grating period) and can once again as a whole be considered as reference path for the complete layout described in the paragraph before the last one (to be interpreted now as signal path). Here the change of the effective refractive index of the other polarization can be measured. (If, however the polarization(s) remains (remain) the same and instead another chemo-sensitive layer (with or without non-specific binding) or a non-specific layer with or without non-specific binding (e.g., dextran layer without identification molecule) is utilized, then the referenced measured values (measured value (first arrangement) measured value (second arrangement)) of the measured values $\Delta N$ (TE) or $\Delta N(TM)$ or $\Delta N(TM)-\Delta N(TE)$ can be determined).

It is also possible, that only the in-coupling grating is present as a chirped grating, the out-coupling grating, however, e.g., is mono-diffractive (or multi-diffractive). The two light spots described three paragraphs above do not anymore travel vertically to the mode propagation direction on the basis of the (bio-)chemical binding, because the out-coupling grating also deflects in the plane of incidence (possibly better referred to as the outlet plane) (i.e., the out-coupling angle changes).

If on the other hand for signal "sensing pad" and reference "sensing pad" one operates with three gratings each (one in-coupling grating and two out-coupling gratings or two in-coupling gratings and one out-coupling grating), whereby modes in forward and reverse directions are excited, if the in-coupling grating is a chirped grating (with the same or with opposite chirp orientation between the two "sensing pads") and if the in-coupling gratings are, e.g., mono-diffractive (or multi diffractive), then displacements or tilting of the x- and y-axis (orientation of the axis as in FIG. 1) can be identified and eliminated on the basis of the absolute measurement. For the chemo-sensitive layer(s), the same remarks are applicable as in the case of the "sensing pad", which consists of two chirped gratings. If, for example, only the (absolute) out-coupling angle (and/or measured values which can be derived from it) are considered as sensor signals, then the chirped in-coupling grating can also be illuminated with a light strip impinging in a wedge-shape. Here too, the above arrangement (signal and reference path) can be duplicated and considered as a new reference path (with or without differing chemo-sensitive layer or with a non-specific layer) to the above arrangement (now as a whole as signal path).

The specimen liquid(s) is (are) brought into contact with the waveguide or with the chemo-sensitive substance(s) through a "well" or a matrix of "wells", a through-flow cell or a matrix of through-flow cells, a capillary vessel or a matrix of capillary vessels (see FIGS. 4-5.

Two-dimensional arrangements lead, e.g., to a "microplate" with 96, 384, 1536 "wells", etc. (But also other two-dimensional formats (e.g., disks) are possible). But also the manufacturing of individual strips (one-dimensional arrangement) is possible. The strips can, e.g., also be inserted into the frame of a microplate. The "wells" can be affixed to the sensorchip plate, which contains the waveguide grating structure units as separate specimen cell (resp., specimen cell plate). It is however, also possible to provide the substrate itself with indentations in such a manner, that these indentations already assume the function of the "wells" or of the through-flow vessels or of the capillary vessels. In the two latter cases, the sensorchip plate has to be covered with a covering plate equipped with bores. In the first case, the sensorchip plate can be covered with a covering plate (without bores), in order to, e.g., prevent evaporation. The bores serve for the supply or carrying away of the specimen or for the ventilation. In preference, one works with plastic material and injection-moulding techniques or hot-embossing techniques. But also sol-gel techniques, UV-hardening techniques for organic/inorganic composites, glass embossing techniques (hot-embossing or (injection-)moulding), etching techniques, material removal by laser, etc., present an alternative.

The grating structures can be manufactured using embossing techniques (hot-embossing, cold-embossing, UV-hardening) or injection-moulding techniques out of plastic material, sol-gel, glass, UV-hardening organic or inorganic materials or organic/inorganic composites, or moceres or nanomeres, with removal by laser in conjunction with interferometry, holography and/or phase mask techniques, photo-lithography in conjunction with wet or dry etching, using photo polymerization (refer to, e.g., P. Coudray et al., Crit. Rev. Opt. Sci. Tech. (SPIE) CR68 (1997), 286-303) or using casting techniques (e.g., in sol-gel), etc. Plastic injection-moulding techniques, such as are utilized in the manufacturing of compact discs (e.g., out of poly-carbonate), are particularly suitable. The grating structure can be in (resp., on) the substrate or in (resp., on) a layer or can be present in a combination of these. The grating structures can be surface relief gratings (resp., interface relief gratings) or refractive-index gratings (resp., volume gratings) or combinations of these. The waveguiding film can be a sol-gel layer ($SiO_2$—$TiO_2$, $TiO_2$, (non-porous) high-refraction lead-silicate glass, etc), an organic/inorganic composite layer, a polymer layer, a PVD-, a CVD-, a PE-CVD-, a PI-CVD layer, a photo-polymerizable, high-refraction layer (e.g., photo-polymerizable $TiO_2$), etc. or combinations of these. It is also possible that a layer (with in preference low refractive index, made, e.g., of $SiO_2$ sol-gel, $SiO_2$—$TiO_2$ sol-gel (with low $TiO_2$ content), lead-silicate glass, sol-gel (with low lead content), sol-gel similar to float-glass, etc.) contains the grating structure and a second layer (e.g., made of $SiO_2$—$TiO_2$, $TiO_2$, $Ta_2O_5$, $HfO_2$, $ZrO_2$, $Nb_2O_5$, $Si_3N_4$, lead-silicate glass, etc.) forms the waveguiding film. Due to the fact that the softening point of lead-silicate glass is significantly below the softening point of glass, the lead-silicate glass can be made to melt without damaging the glass in doing so. The melting process leads to a practically pore-free lead-silicate glass. If the substrate and the layer(s) have similar thermal expansion coefficients, then the formation of micro-fissures can be prevented (micro-fissures increase the dampening values of the modes). PVD- and CVD-processes make possible the manufacture of very compact waveguiding films.

The substrate can be made of a plastic material (e.g., poly-carbonate, PMMA, polystyrene, etc.), sol-gel or of glass (float-glass, specimen slides, soda-lime glass, boro-silicate glass, alkali-free glass, quartz, etc,). However, also the grating material can be utilized as substrate material (e.g., ormocere, UV-hardening material).

The specimen cell can consist of indentations (holes, bores), also, however, of through-flow cells. These through-flow cells can also be configured in such a manner, that the specimen liquid can be supplied using the pin of a pipette robot. It is also possible, that a second specimen cell consisting of through-flow vessels is inserted into a first specimen cell with indentations (holes).

In the substrate or anywhere on the sensorchip plate, positioning marks (holes, indentations, pins, elevations, etc.) can be inserted or affixed. These positioning marks guarantee that the impinging light beam hits the in-coupling grating(s). The identification of the positioning marks is effected through the measuring unit.

For the separation of the light wave carrying the sensor signal from other light waves (e.g., from the light wave reflected from the bottom of the substrate), it is also advantageous if the waveguiding film is not plane-parallel to the bottom of the substrate. This non-plane-parallelism can be present, among others, in the form of wedges, prisms, cylinder prisms, spherical lenses, cylinder lenses, etc.

With the chemo-sensitive waveguide structure, not only a direct detection, but also marking detections can be carried out. The utilization of a "refractive index label" (e.g., of a little plastic ball (e.g., a small latex ball), bio-chemical and biological fragments, etc.), can already be considered as a marking detection. With it, for example, sandwich assays or competition assays can be implemented.

As light source a monochromatic light source, such as, e.g., a (pulsed) laser, a (pulsed) laser-diode, a (pulsed) LED with or without filter in the (infra)red or blue-green or ulta-violet spectral range, is advantageously used. But also thermal light sources with a filter can be utilized. Red-blue-green or ultra-violet wavelengths have the advantages that (a) the sensitivity for the direct detection increases and (b) with the same light source apart from "direct sensing" also fluorescence-, phosphorescence or luminescence tests can be conducted, whereby the excitation of the fluorescence, phosphorescence or luminescence takes place through the evanescent wave (in the form of a TE-wave or TM-wave or TE- and TM-wave). The fluorescence-, phosphorescence- or luminescence-light can be observed as a plane wave or also as a guided wave. The fluorescent light caused by the TE-exciting wave (resp., its intensity) can be referenced or compared with the fluorescent light (resp., its intensity) caused by the TM-exciting wave, whereby advantageously the intensity of the exciting wave is jointly taken into account and possibly the detectors are made sensitive to polarization by the utilization of polarizers. The guided fluorescence-, phosphorescence- or luminescence-light wave can be out-coupled through a grating and conveyed to a detector. Sandwich-assays, competition assays, etc., can be carried out, whereby at least one participating binding partner is fluorescence- (phosphorescence-, luminescence-) marked. The (bio-) chemosensitive layer can be present on the grating, or can also, however, be present solely between the gratings or outside the grating.

Fluorescence, phosphorescence or luminescence measurements manifest a low dependence on temperature. For fluorescence, phosphorescence or luminescence measurements, purely inorganic waveguide grating structures are particularly suitable (the grating is manufactured in glass or sol-gel (e.g., $SiO_2$) or in the inorganic waveguiding film, waveguiding film made of inorganic material (e.g., $Si_3N_4$ or oxide layers such as, e.g., $TiO_2$ or $Ta_2O_5$ or lead-silicate layers, etc.)). Inorganic materials manifest, e.g., a low fluorescence of their own. If one works with a plastic material substrate, then it is recommended to apply an inorganic low-refraction intermediate layer (e.g., $SiO_2$) to the plastic substrate. The layer thickness of this intermediate layer has to be selected as great enough, so that the evanescent wave running in it practically does not anymore "see" the plastic substrate. As a result of this, at least the proprietary fluorescence generated by the guided light wave is strongly reduced.

If both the intensity of the (possible out-coupled) excitation wave as well as that of the (possibly out-coupled) emission wave are measured, then various interference factors (such as, e.g., those, which are caused by intensity fluctuations of the exciting wave) can be eliminated by referencing. The referenced sensor signal is then, for example, the intensity of the fluorescence (phosphorescence, luminescence) divided by the intensity of the exciting light wave. The intensity of the exciting wave can be measured prior to the penetration of the exciting wave into the chemo-sensitive layer or after the exit of the exciting wave from the chemo-sensitive layer or at both points. With referenced marking detections, absolute kinetic measurements as well as absolute end point measurements can be carried out. In the case of absolute (end point) measurements, the (bio-)chemical interaction on the waveguide grating structure can also take place outside the measuring instrument.

It is also to be noted that with a (digital or analogue) PSD (position sensitive detector) (one-dimensional or two-dimensional), a photo-diode-array (PDA) (one-dimensional or two-dimensional) or a CCD-array (one-dimensional or two-dimensional), not only (positions of) light field distributions but also intensities can be measured.

It is possible (but it is not absolutely necessary) to in part with the same detectors carry out a direct detection as well as a marking detection (on a fluorescence, phosphorescence or luminescence basis). Evanescence field excitation can also be combined with measuring techniques resolved over time (e.g., time-resolved fluorescence or luminescence). In the case of time-resolved measuring techniques, the marking is excited with a pulsed light wave (primarily in the visible or ultra-violet wavelength range). The fading times for the fluorescence (luminescence, phosphorescence) of free and bound marking molecules (with or without energy transfer between two different fluorescence molecules (refer to, e.g., the Förster theory in CIS Bio International, November 1995, No. 3)) are different. The depth of penetration of the guided excitation wave into the specimen determines the "observation volume".

It is interesting that with the waveguide grating structures presented here absolute measurements can be carried out both free of marking as well as fluorescence (phosphorescence, luminescence) marked (if so required also simultaneously). In both cases, for the in-coupling of light one can make do without movable mechanics. It goes without saying that also (continuous) kinetic measurements or real-time measurements can be carried out on a non-absolute basis.

With a "sensing pad" (signal path) (with or without chemo-sensitive layer), it is also possible to carry out light absorption measurements, inasmuch as the intensities of the light beams out-coupled (through grating, prism, taper or front side) (if so required with the same detectors) can be measured, possibly also at different wavelengths. The change in light absorption can come about directly or indirectly (e.g., through enzymes) through the (bio-)chemical interaction of the specimen with the chemo-sensitive layer or through the specimen itself or through the reactions taking place in the specimen (with or without an additional reaction partner). The chemo-sensitive layer can be present on the grating, between the gratings or outside the grating. Fluctuations in light intensity of the light source can be eliminated by referencing (e.g., with a beam-splitter and a reference detector or through a not in-coupled diffraction order and a reference detector). Referencing can also be carried out by the method in which the second "sensing pad" (reference path) is covered with a protective layer and therefore cannot interact with the specimen. The referenced sensor signal is then the intensity of the signal path detector divided by the intensity of the reference path detectors.

The protective layer, however, can also be a (porous) (chemo-sensitive) layer, which has no specificity (with or without "non-specific binding") or specificity for another ligand.

Referencing can also (but does not have to) take place through one half of a "sensing pad" (e.g., signal path: mode in forward direction, reference path: mode in reverse direction).

What is claimed is:

1. An optical sensor comprising an optical waveguide which includes a substrate, a waveguiding material, a cover medium and at least one waveguide grating structure, where each waveguide grating structure includes two sensing pads where one is a sensing pad and the other is a reference sensing pad, wherein said sensing pad is coated with a first chemo-sensitive layer to which a specific binding partner binds, and wherein said reference sensing pad is coated with a second chemo-sensitive layer to which the specific binding partner does not bind, wherein a well or a matrix of wells is arranged on the at least one waveguide grating structure or in the at least one waveguide grating structure.

2. The optical sensor according to claim 1, wherein the sensing pad and the reference sensing pad are adjacent to one another.

3. The optical sensor according to claim 1, wherein the sensing pad and the reference sensing pad are arranged at least partially in a distance from each other.

4. An optical sensor comprising an optical waveguide which includes a substrate, a waveguiding material, a cover medium and at least one waveguide grating structure, where each waveguide grating structure includes two sensing pads where one is a sensing pad and the other is a reference sensing pad, wherein said sensing pad is coated with a first chemo-sensitive layer to which a specific binding partner binds, and wherein said reference sensing pad is coated with a second chemo-sensitive layer to which the specific binding partner does not bind, wherein a flow-through cell or a matrix of flow through cells or a capillary vessel or a matrix of capillary vessels are arranged on the at least one waveguide grating structure or in the at least one waveguide grating structure.

5. The optical sensor according to claim 4, wherein the sensing pad and the reference sensing pad are adjacent to one another.

6. The optical sensor according to claim 4, wherein the sensing pad and the reference sensing pad are arranged at least partially in a distance from each other.

* * * * *